(12) United States Patent
Österdahl et al.

(10) Patent No.: US 7,048,124 B2
(45) Date of Patent: May 23, 2006

(54) PACKAGING UNIT

(75) Inventors: Eje Österdahl, Västra Frölunda (SE);
Pontus Winqvist, Stora Höga (SE);
Roy Hansson, Mölndal (SE)

(73) Assignee: SCA Hygiene Products AB,
Gothenburg (SE)

( * ) Notice: Subject to any disclaimer, the term of this patent is extended or adjusted under 35 U.S.C. 154(b) by 0 days.

(21) Appl. No.: 11/025,061

(22) Filed: Dec. 30, 2004

(65) Prior Publication Data

US 2005/0155888 A1      Jul. 21, 2005

Related U.S. Application Data

(60) Provisional application No. 60/532,950, filed on Dec. 30, 2003.

(51) Int. Cl.
*B65D 71/06*      (2006.01)
(52) U.S. Cl. ....................... 206/494; 604/358
(58) Field of Classification Search ................ 206/440, 206/494, 497, 499, 812; 604/358, 387, 385.01–385.05, 604/368, 385.201, 385.21–385.23
See application file for complete search history.

(56) References Cited

U.S. PATENT DOCUMENTS

| 5,361,905 A * | 11/1994 | McQueeny et al. ......... 206/494 |
| 5,934,470 A * | 8/1999 | Bauer et al. ................ 206/494 |
| 2004/0134822 A1* | 7/2004 | Otsubo ....................... 206/494 |

FOREIGN PATENT DOCUMENTS

| EP | 0 122 042 A2 | 10/1984 |
| EP | 0 391 460 A1 | 10/1990 |
| EP | 0 406 928 A1 | 1/1991 |
| EP | 0 778 015 A1 | 6/1997 |
| EP | 0 780 325 A1 | 6/1997 |
| EP | 0 947 446 A1 | 10/1999 |
| EP | 1 205 171 A2 | 5/2002 |
| GB | 2 264 278 A | 8/1993 |
| WO | WO 93/16925 A1 | 9/1993 |
| WO | WO 97/33815 A1 | 9/1997 |

* cited by examiner

*Primary Examiner*—Luan K. Bui
(74) *Attorney, Agent, or Firm*—Buchanan Ingersoll PC

(57) ABSTRACT

A packaging unit for absorbent articles including a number of folded absorbent articles arranged with their folded edges placed head to tail in the packaging unit, the folded edges arranged at a first side of the packaging unit being situated at different distances from the first side, and the folded edges arranged at the opposite side of the packaging unit being situated at different distances from the opposite side.

17 Claims, 7 Drawing Sheets

PACKAGING UNIT

CROSS-REFERENCE TO RELATED APPLICATION

The present application claims the benefit of U.S. Provisional Application No. 60/532,950, filed in the United States on Dec. 30, 2003, the entire contents of which are hereby incorporated herein by reference.

TECHNICAL FIELD

The present invention relates to a packaging unit comprising a first side and an opposite second side. The packaging unit comprises a number of folded absorbent articles, each absorbent article having a front end portion, a rear end portion, and a crotch portion arranged between the end portions. The articles further comprise absorption bodies, each absorption body comprising a front transverse edge arranged at the front end portion of the article, and a rear transverse edge arranged at the rear end portion of the article. Each article is folded along a substantially transverse fold line arranged in the crotch portion, each article having a fold area, and a number of the articles are oriented with their fold areas at the first side of the packaging unit, and the remaining articles in the packaging unit are oriented with their fold areas at the second side of the packaging unit.

BACKGROUND

In the technical field of absorbent articles, considerable efforts have been made over many years to increase the number of manufactured articles, for example babies' diapers or incontinence diapers, per unit of volume for storage and transportation. Nowadays, for example, twice as many babies' diapers are transported by truck as were transported in a similarly sized truck a number of years ago.

Thinner articles, still with a high absorption capacity, represent one of the areas that have been improved. Enhanced thinness has been achieved principally by introduction of gel-forming polymers, called superabsorbents, in increasing concentrations in the absorption cores of the absorbent articles. The articles have in this way been improved in terms of their handling both during storage and transportation. Thinner absorbent articles have also been preferred by users, and this fact has of course also prompted various manufacturers to steer developments in this direction.

Thinness has also been achieved by the fact that the articles are nowadays compressed much more than in the past. EP 0,122,042 is one example of a patent which describes how absorbent articles are compressed efficiently so as to achieve increased thinness while at the same time maintaining or even improving the absorption capacity. Specifically, EP 1,122,042 discloses compressing absorption bodies at a low moisture content in order to maintain softness and pliability despite compression to high density levels (low bulk levels).

More effective ways of packaging absorbent articles have also been developed. The absorbent articles have been packaged with ever greater compression. The most common way of introducing a stack of absorbent articles into a bag has involved use of a special gripping device, which is allowed to compress the stack of diapers and is introduced into the bag together with said diapers. The gripping device has been designed in such a way that it has been possible to remove it from the bag when the stack has been correctly positioned in the bag.

Patent application GB 2,264,278 A describes a method for effective compression of a stack, that is to say an individual packaging unit, of absorbent articles in connection with the articles being enclosed in a band-shaped wrapper. The volume of the packaging is minimized by means of a stack of folded absorbent articles being compressed together with a two-part packaging envelope of the wrapper type. Finally, the absorbent articles are locked in the compressed state by the two parts of the packaging envelope being connected to one another when the absorbent articles are still under external compression.

EP 0,780,325 B1 describes an improved method of configuring a packaging unit, in which the folded absorbent articles have been arranged head to tail. Configuring the articles in this way in the packaging unit permits harder compression of certain types of absorbent articles in the packaging unit. The method of forming a packaging unit in said patent works best for articles which have different amounts of absorption material, that is to say different thicknesses, at their waist areas compared with the thickness at their crotch areas, which situation is relatively common. The differences in thickness between waist area and crotch area are compensated by the fact that the packaging unit has the same number of waist areas as crotch areas at the opposite surfaces in the packaging unit. The end result is a packaging unit which has uniform thickness at its opposite surfaces where the crotch areas and waist areas of the absorbent articles are alternately arranged. The packaging unit can thus be compressed and acquires increased density in, for example, a bag, without the bag having a parallel trapezoid shape.

A problem which is only partially solved in EP 0,780,325 B1 is that of protecting the folded areas at the crotch areas of the articles when the packaging unit is compressed.

When a packaging unit comprising absorbent articles folded once about a substantially transverse fold line is compressed at right angles to the material layers, the fold area is the most sensitive area of the article. High compression often means that permanent fold notches are formed, and the absorbent article will then have a hard and uncomfortable crease when it is being worn by a user. Fold notches also function as channels in which liquid can run, a fact which is particularly unfortunate when the channels extend in the transverse direction of the absorbent article and are located in the area where various body fluids such as urine are collected in the absorbent article.

Compression of other parts of the absorbent articles in the packaging unit, that is to say compression at right angles to the material layers, is not as problematic because no creases or the like are created. In addition, the material layers normally included in absorbent articles have a considerable capacity for recovering their original configuration when the compression ceases, as long as the compression has taken place at right angles to the material layers.

There is therefore still a need for a packaging unit in which the fold areas of the absorbent articles are better protected when the packaging unit is compressed in connection with introduction of the articles into a bag, for example, or upon compression in connection with enclosure in a wrapper.

SUMMARY OF THE INVENTION

A packaging unit of the type mentioned in the introduction has been obtained with the present invention, which packaging unit to a large extent avoids the problems which were associated with previously known packaging units.

A packaging unit formed according to a preferred embodiment of the present invention is distinguished principally by the fact that the number of front transverse edges of the absorption body plus the number of rear transverse edges of the absorption body at the first side of the packaging unit is at most equal to about 120% of the number of fold areas at the first side of the packaging unit, and that the number of front transverse edges of the absorption body plus the number of rear transverse edges of the absorption body at the second side of the packaging unit is at most equal to about 120% of the number of fold areas at the second side of the packaging unit.

By this method of configuring the articles in the packaging unit, it is possible to avoid a situation where permanent fold notches are created when the articles are pressed together hard during packaging in a bag, for example. Greater packaging density with improved utilization of volume during storage and transportation without the aforementioned disadvantages is therefore an important result of the invention.

A packaging unit for absorbent articles in accordance with the invention thus comprises a number of folded absorbent articles arranged with their folded edges head to tail in the packaging unit, the folded edges arranged at one side of the packaging unit being situated at different distances from said side, and the folded edges arranged at the opposite side of the packaging unit being situated at different distances from said opposite side.

According to a second embodiment of the packaging unit, the absorbent articles in the packaging unit are folded about substantially transverse fold lines arranged substantially at the centre of the absorption bodies in the longitudinal direction of the absorption bodies. The articles oriented with their substantially transverse fold lines at the first side of the packaging unit are offset in a direction away from the second side of the packaging unit, and articles oriented with their substantially transverse fold lines at the second side of the packaging unit are offset in a direction away from the first side of the packaging unit.

According to an alternative embodiment of a packaging unit according to the invention, the absorbent articles in the packaging unit are folded about substantially transverse fold lines situated at a distance from the centre of the absorption bodies in the longitudinal direction of the absorption bodies. In this case, only one of the front transverse edge and rear transverse edge of the respective article's absorption body is arranged at either the first or second side of the packaging unit.

According to a preferred embodiment of the invention, every second folded article is oriented with its substantially transverse fold line at the first side of the packaging unit, and every other folded article is oriented with its substantially transverse fold line at the second side of the packaging unit.

Further, in a preferred embodiment of the invention, the articles in the packaging unit are arranged in subunits. All the articles in a subunit are arranged with their substantially transverse fold lines at the same side in the packaging unit. Subunits adjacent to one another are arranged with the substantially transverse fold lines of their articles at different sides of the packaging unit.

Each subunit comprises two to four articles, preferably two articles according to a preferred embodiment of the present invention.

In accordance with a preferred embodiment, the absorbent articles which are arranged with their fold lines at the first side of the packaging unit are offset by a distance of about 5–30 mm, preferably 5–15 mm, in relation to articles arranged with their fold lines at the second side of the packaging unit.

According to another preferred embodiment, the substantially transverse fold lines of the absorbent articles are situated at a distance from the centre of the absorption bodies in the longitudinal direction of the absorption bodies, so that the distance between the front transverse edge and the rear transverse edge of the absorption bodies is about 5–30 mm, preferably 5–15 mm, when the article is folded.

Also in accordance with a preferred embodiment, the packaging unit is packed in a bag, and in one embodiment, the packaging unit is enclosed in a band-shaped wrapper.

Packaging units according to the present invention may contain babies' diapers, incontinence diapers for adult users, sanitary napkins, or the like.

BRIEF DESCRIPTION OF THE FIGURES

The present invention will be described in greater detail below with reference to the figures shown in the attached drawings.

DETAILED DESCRIPTION OF THE PREFERRED EMBODIMENTS

Figure 1:
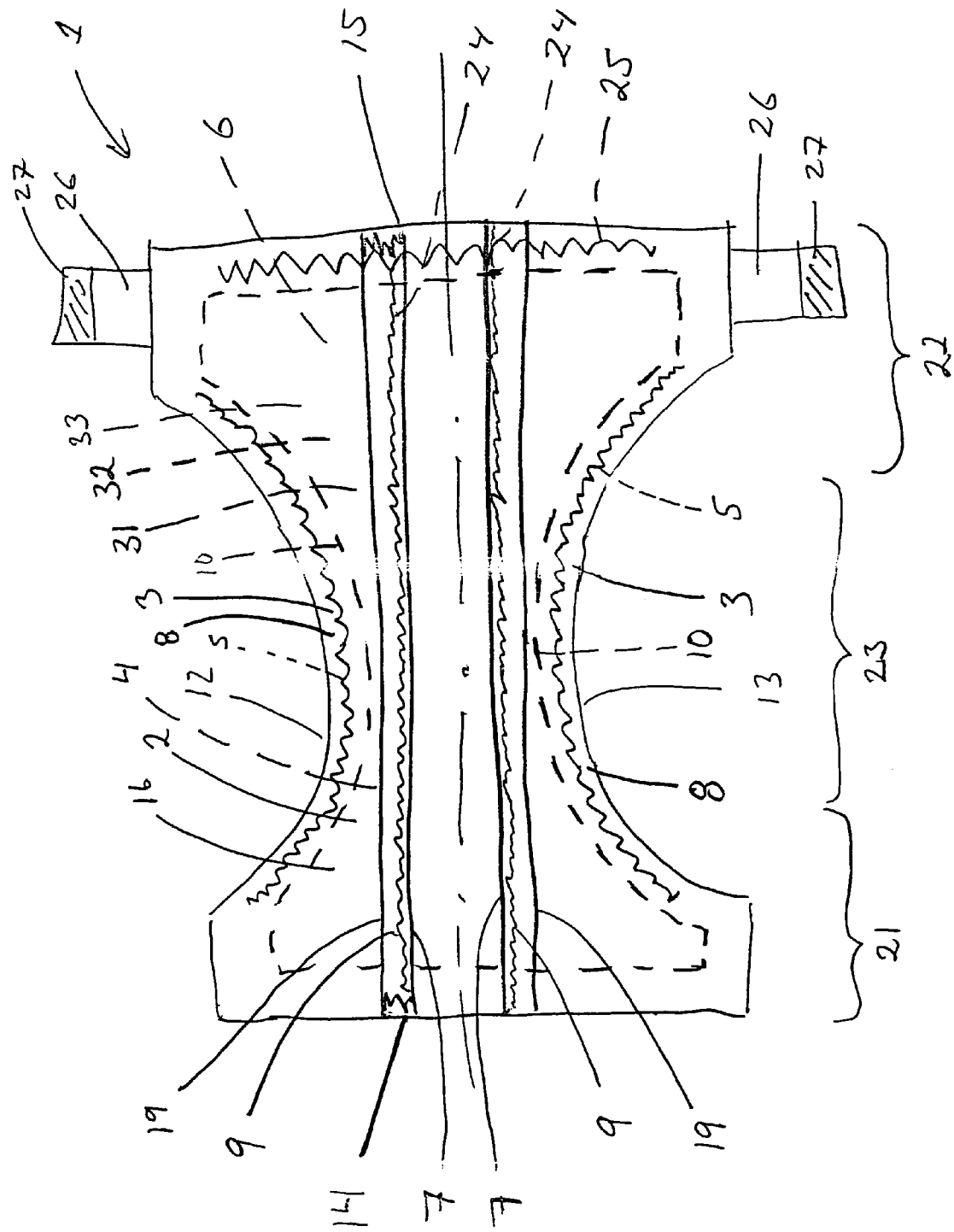
FIG. 1 shows an example of a diaper which can be included in a packaging unit according to the present invention.

The present invention concerns a packaging unit 17, shown in FIGS. 3–6 and comprising a number of folded absorbent articles 1.

Absorbent articles 1, included in packaging units 17 according to the present invention, can be so-called all-in-one diapers, pant diapers, belt diapers, sanitary napkins, or the like.

So-called pant diapers are primarily distinguished by the fact that they have already been folded, at the time of production, about a substantially transverse fold line 41 in the crotch portion 23 of the diaper, and have then been joined together at the waist. The area near the fold line 41 constitutes the fold area 11 of the pant diapers. This type of diaper is intended to be applied on a user exactly like a pair of briefs, that is to say pulled up over the legs.

Belt diapers generally comprise, in relation to the absorbent part of the diaper, a transverse belt connected either to the front or rear transverse edge of the diaper. When applying such a belt diaper, the belt is fixed, in a first step, around the user's waist. The absorbent part of the diaper is at this stage hanging loosely from the belt. The absorbent part of the diaper is thereafter guided between the user's legs and secured to the belt, said belt comprising fixing surfaces intended to adhere firmly to the fixing devices arranged on the absorbent part of the diaper near its free transverse edge.

The present invention is of course applicable both to babies' diapers and to adults' diapers or incontinence garments of the various types described above. The invention can also be applied to absorbent articles intended for menstruation which are designed to be packaged and sold in the folded state.

FIG. 1 shows the main components of an exemplary diaper 1 suitable for inclusion in a packaging unit according to the invention. The diaper 1 is an open diaper for babies and of the so-called all-in-one type. The diaper 1 is in this case not joined together at the waist portion when sold, and instead is designed to be applied round a baby's trunk and thereafter joined together around the waist.

The diaper 1 is preferably substantially hourglass-shaped and has longitudinal edges 12, 13, a front transverse edge 14, and a rear transverse edge 15, and front and rear end portions 21, 22, and a narrower crotch portion 23 located between the end portions 21, 22. During use, the crotch portion 23 is intended to be located at the narrowest area between the baby's thighs.

When the diaper 1 is in use, the front part of the crotch portion 23 and the front end portion 21 function principally as a receiving area for urine, while the rear part of the crotch portion 23 and the rear end portion 22 principally function as a receiving area for faeces.

The diaper 1 preferably comprises a covering sheet 16 having a liquid-permeable covering sheet 2 arranged over that surface of the diaper 1 which during use is intended to face towards the baby, and a liquid-impermeable backing sheet 4 arranged over that surface of the article which during use is intended to face away from the baby, an absorption body 6 enclosed between the liquid-permeable covering sheet 2 and the backing sheet 4, and side flaps 3 arranged outside the absorption body 6.

The liquid-permeable covering sheet 2 preferably extends outside the absorption body 6 along the whole periphery of the absorption body 6. The liquid-permeable covering sheet 2 may be formed from any material suitable for the purpose. Examples of commonly used liquid-permeable covering materials are nonwoven textile materials, perforated plastic films, plastic netting or textile, and liquid-permeable foam sheets. Liquid-permeable covering sheet materials may also have continuous thin fibres extending substantially in the longitudinal or transverse direction of the article. Laminates including two or more of the above-mentioned possible covering materials are also commonly used, as well as covering sheets having different materials within different parts of the surface.

Diapers 1 which have absorption bodies 6 having particularly high strength and resistance to wear can even function without any extra liquid-permeable covering sheet being required on that side of the diaper which faces towards the baby during use.

The backing sheet 4 preferably includes a laminate 31 comprising a liquid-impermeable plastic film 32 arranged towards the absorption body 6 and a nonwoven sheet 33, said nonwoven sheet 33 being arranged away from the absorption body 6 so that the outside of the diaper 1 is more like clothing during use of the diaper 1. The backing sheet 4 preferably extends outside the absorption body 6 along the entire periphery of the absorption body 6.

The backing sheet 4 of babies' diapers 1 usually includes liquid-impermeable plastic films or laminates in which liquid-impermeable plastic films are included, but other types of liquid-impermeable backing sheets are also possible. Examples of alternative types of liquid-impermeable materials are nonwoven materials which have been made liquid-impermeable, liquid-impermeable foam sheets, liquid-impermeable adhesive, or similar. Nowadays it is also common for the backing sheet 4 to have a vapour-permeable plastic film, or a laminate in which a vapour-permeable plastic film is included as a liquid barrier. The vapour-permeable plastic film should of course also be liquid-impermeable in order to prevent passage of liquid from the absorption body. The nonwoven sheet 33 can be designed so that it functions as a receiving sheet for the male component of a hook-and-loop system. The nonwoven sheet 33 in this case comprises closed loops or the like.

In a preferred embodiment, the liquid-permeable covering sheet 2 and the backing sheet 4 are connected to one another outside the absorption body 6, along the entire periphery of the absorption body 6. The connection between the sheets 2, 4 can be effected in a number of different ways. Examples of connection methods are gluing, melt-bonding, ultrasonic welding, or similar.

Elastic members 5 are preferably arranged outside the absorption body 6 in those parts of the side flaps 3 of the disposable diaper 1 which substantially extend in the longitudinal direction of the diaper 1. The elastic members 5 function as leg elastics and have the role of substantially preventing liquid and excrement from leaking out through the longitudinally extending side edges 12, 13 and in this way they form outer liquid barriers 8 in conjunction with the surrounding layers. The elastic members 5 include one or more elastic threads which, in the stretched state, have been applied between the liquid-permeable covering sheet 2 and the backing sheet 4, at least in the crotch portion 23 of the diaper 1. The elastic members 5 are connected to the backing sheet 4 and the covering sheet 2 by gluing, ultrasonic welding or similar.

In alternative embodiments, the elastic members can be arranged on that side of the side flaps 3 which is intended to face towards the user during use, or on the opposite side of the side flaps, and are of course then only connected to the liquid-permeable covering sheet 2 or the backing sheet 4.

In alternative embodiments, the elastic members can comprise elastic band material, for example made of foam material.

The hourglass-shaped absorption body 6 may be made up of one or more layers of cellulose fluff pulp. The cellulose fluff pulp can be mixed with fibres or particles of a superabsorbent polymer material of the type which chemically binds large amounts of liquid upon absorption, thus forming a liquid-containing gel. The absorption body 6 may also comprise superabsorbent polymer material arranged in a layer inside the absorption body or near the surface or surfaces of the absorption body. The absorption body 6 can also include further components for improving the properties of the absorption body 6. Examples of such components are binder fibres, various types of liquid-spreading layers or fibres, shape-stabilizing components, reinforcement fibres, or similar. The absorption body 6 may of course also have other types of absorption material, such as absorbent nonwoven material, absorbent foam, textile material, peat, or mixtures of various types of absorption material.

Diapers of the type in question may also include special layers for rapidly taking up a large amount of liquid and temporarily storing it before passing the temporarily stored liquid to other parts of the absorption body 6. Such receiving layers are normally arranged between the liquid-permeable covering sheet 2 of the diaper 1 and the absorption body 6, but are not shown in any of the present figures.

To further prevent liquid or faeces from leaking out via the side edges 12, 13 of the diaper 1, said diaper 1 is preferably provided with inner side leakage barriers 9 on the side intended to face towards the baby during use. The inner side leakage barriers 9 are preferably arranged lying near the longitudinal edges 10 of the absorption body 6 and extend substantially in the longitudinal direction of the diaper 1. The side leakage barriers 9 are made of double-folded separate material strips, the fold edges 7 constituting the ridges of the side leakage barriers 9. The branches of the double-folded material strips are fixed to the covering sheet 2 and constitute fixed edges 19 of the side leakage barriers. In the front end portion 21 and rear end portion 22 of the diaper 1, the side leakage barriers 9 are turned down and connected to the covering sheet 2 across their entire widths.

The inner side leakage barriers 9 further include elastic elements 24 connected to the inner side leakage barriers 9 in the tensioned state. The elastic elements 24 are preferably arranged near the free edges of the side leakage barriers 9. When the tensioned elastic elements 24 are released, they contract together with the free edges of the side leakage barriers 9, and the inner side leakage barriers 9 are thus brought into a raised configuration directed away from the liquid-permeable covering sheet 2 in the crotch portion 23 of the diaper 1, where the side leakage barriers 9 are preferably only connected to the covering sheet 2 at their respective fixed edges 19.

The rear and/or front portions 22, 21 of the diaper 1 can also be provided with so-called waist elastic 25 which includes elastic devices arranged along the front transverse edge 14 and/or rear transverse edge 15 of the diaper 1 in order to allow the diaper to close gently and flexibly about the user's waist. In the present illustrative embodiment, only the rear end portion 22 of the diaper 1 is provided with waist elastic 25 in the form of a thin strip of an elastic foam material which is fixed with glue between the backing sheet 4 and the liquid-permeable covering sheet 2. The waist elastic 25 is preferably applied in the stretched state between the layers in order to generate a holding force stretching the diaper 1 about the user's waist.

The rear end portion 22 is provided with two soft and non-elastic fastening tabs 26 for fixing the diaper 1 about the baby's waist, with one fastening tab 26 arranged on each side portion of the rear end portion 22. The fastening tabs 26 are expediently made of a very soft and non-elastic material, for example a single nonwoven layer or a laminate. During use, the fastening tabs 26 connect the rear end portion 22 to the front end portion 21.

The fastening tabs 26 further include fixing devices 27, said fixing devices 27 preferably having a male part of a hook-and-loop system and being secured to the fastening tabs 26 with glue or the like. The fixing devices 27 are arranged on that side of the respective securing tab 26 which faces towards that surface on the front end portion 21 which faces away from the baby during use.

In alternative embodiments, the securing tabs 26 can be elastic. The fixing devices 27 of the securing tabs 26 can, in some embodiments, include female parts of a hook-and-loop system, pressure-sensitive adhesive or the like.

When applying the diaper 1 about a baby's waist, the rear end portion 22 is coupled to the front end portion 21 by connecting the fixing devices 27 of the securing tabs 26 to the front end portion 21. Since the diaper 1 has a backing sheet 4 comprising a nonwoven layer 33 functioning as receiving layer for a hook-and-loop material of the male type, the fixing device 27 can be secured anywhere on the backing sheet 4 of the diaper 1.

For alternative embodiments in which the backing sheet 4 of the diaper 1 is not adapted to cooperate with the fixing devices 27 of the securing tabs 26, special fixing sites are expediently arranged on the backing sheet 4 of the diaper 1 in the front end portion 21. The special fixing sites in this case are preferably separate material sections of suitable shape and size, said material sections comprising material that can be connected to the fixing devices 27 of the securing tabs 26. The separate material sections are applied on the backing sheet 4 by gluing, thermal welding, ultrasound welding or similar. The fixing sites are preferably arranged parallel to and close to the front transverse edge 14 of the diaper 1.

Diapers 1 which comprise fixing devices 27 of the adhesive type, and whose backing sheet 4 comprises a nonwoven layer 33, normally have special fixing sites in the front end portion 21 which are designed for receiving adhesive fixing devices 27. Special fixing sites can comprise a plastic surface or the like and usually include one or more separate material sections of suitable shape and size which have been applied at suitable sites on the backing sheet 4 by gluing, thermal welding, ultrasound welding or the like.

It is also common for diapers 1, equipped with adhesive fixing devices 27, to have a backing sheet 4 which only includes a plastic film or the like, in which case the adhesive fixing device 27 can be secured directly to the backing sheet 4 of the diaper 1 anywhere on the backing sheet 4.

Figure 2:
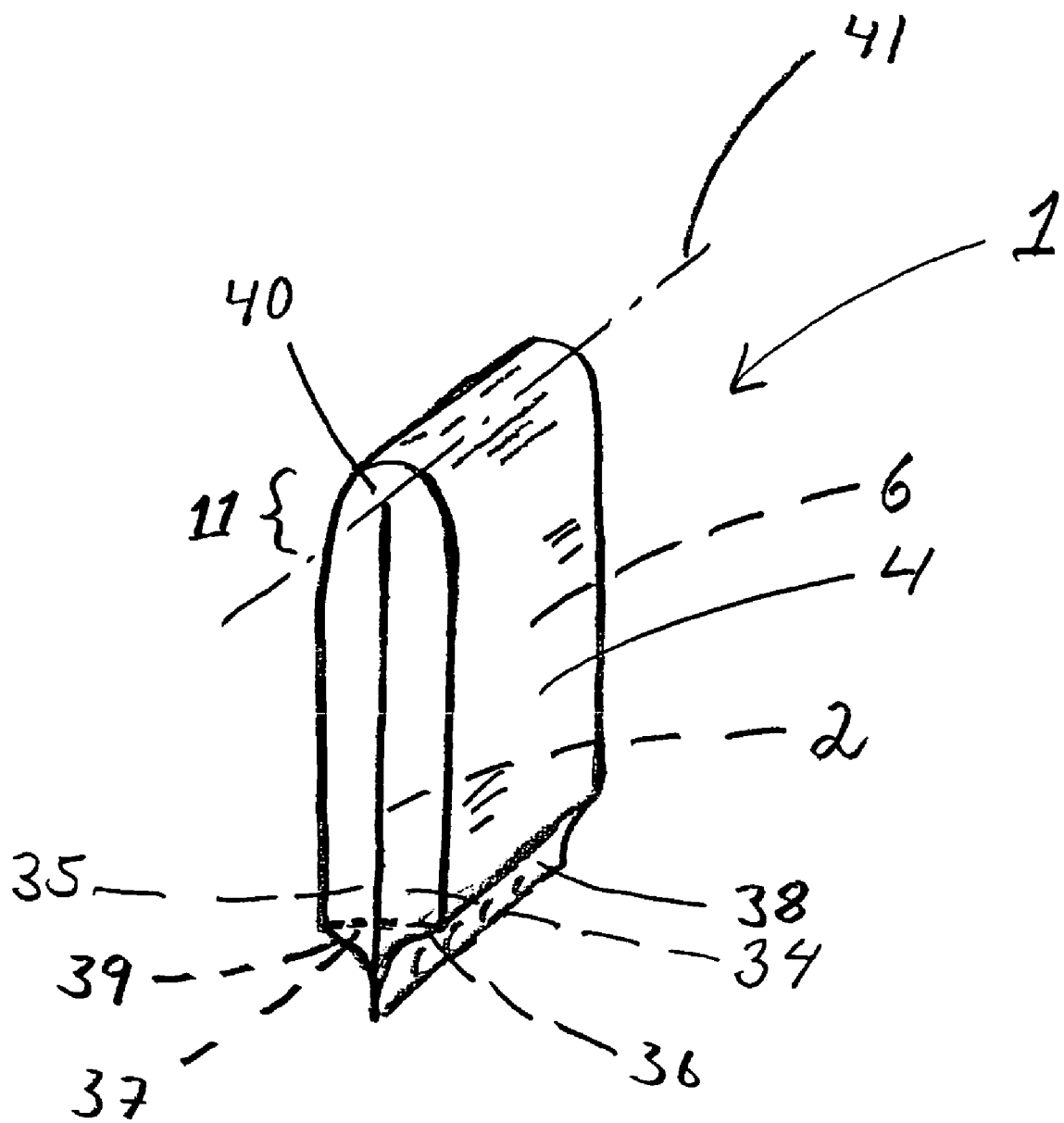
FIG. 2 shows a diaper configured for inclusion in a packaging unit according to the present invention.

FIG. 2 shows a diagrammatic illustration of a diaper 1 configured in the same way as the diapers 1 included in a packaging unit 17 according to the present invention. The diaper 1 is folded in half, substantially along a transverse fold line 41, said fold line 41 preferably being arranged substantially at the centre of the diaper 1, in the longitudinal direction of the diaper 1. A fold area 11 near the fold line 41 is thus defined in the diaper 1.

The diaper 1 is shown diagrammatically, and some of the components of the diaper 1 have been omitted for clarity. Examples of components not included in FIG. 2 are securing tabs 26 and waist elastic 25.

The absorption body 6 has a fold area 40 which coincides with the fold area 11 of the diaper. The absorption body 6 has a front transverse edge 36 and a rear transverse edge 37. The front end seal 38 of the diaper 1 is preferably arranged outside the front transverse edge 36 of the absorption body 6, and the rear end seal 39 of the diaper 1 is preferably arranged outside the rear transverse edge 37. The end seals 38, 39 comprise the liquid-permeable covering sheet 2 and the backing sheet 4, said two sheets 2, 4 being connected to one another by gluing. In alternative embodiments, the end seals 38, 39 can be arranged in an alternative way, for example a separate covering sheet arranged outside the backing sheet can be included in the end seals 38, 39.

The absorption body 6, which represents the greatest part of the thickness of the diaper 1, is principally made from what is called airlaid fluff pulp, and which is especially sensitive to permanent fold notches being created if it is pressed together hard where the fluff pulp is folded.

The most common situation, especially for smaller diapers 1 intended for babies, is that they are folded along a transverse fold line 41, substantially at the centre of the diaper 1 in its longitudinal direction, when they are being packaged. The fold area 11 around the fold line 41 is thus sensitive to formation of permanent fold notches when the diaper 1 is exposed to strong compression at right angles to its material during packaging of the diaper 1. An especially disadvantageous combination as regards formation of permanent fold notches is strong compression of the diaper 1 in combination with a high moisture content, that is to say a moisture content in excess of 10%.

When a diaper 1 which has been compressed strongly during packaging is later removed from its package at the time of use, it is not uncommon for the diaper 1 to have a permanent and hard fold notch located in that part of the diaper 1 normally placed in the user's crotch area during use of the diaper 1.

Figure 2A:
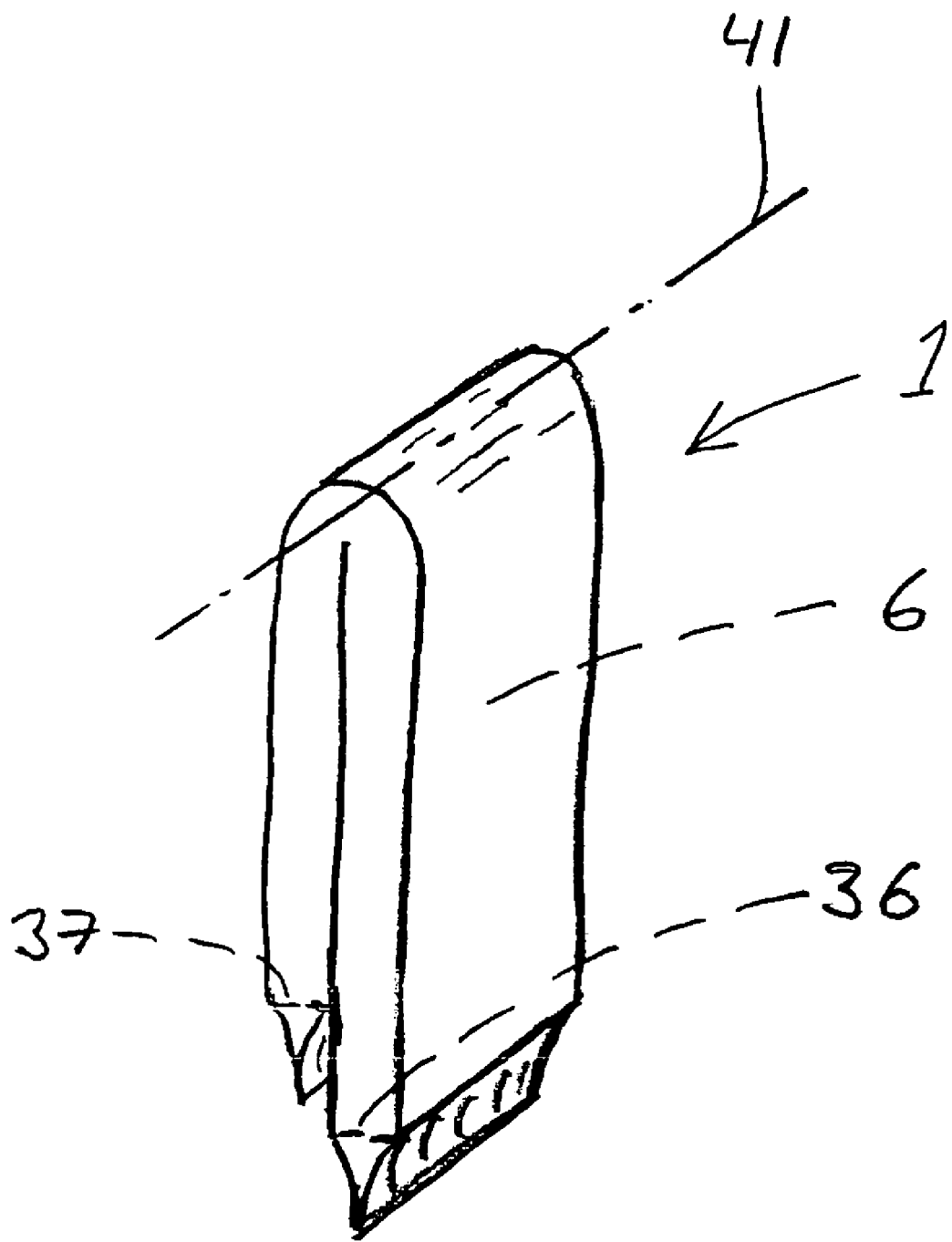
FIG. 2a shows a diaper differently configured for inclusion in a packaging unit according to the present invention.

FIG. 2a shows a diagrammatic illustration of a diaper 1 configured in the same way as the diapers 1 included in an alternative packaging unit 17 according to the present invention. This diaper 1 is also folded in half (i.e., in two) along a substantially transverse fold line 41. The fold line 41 is in this case arranged at a distance from the centre of the diaper 1, in the longitudinal direction of the diaper. This folding method means that the front transverse edge 36 of the absorption body 6 ends a greater distance from the rear transverse edge 37 of the absorption body 6. Alternatively, the folding can be arranged so that the rear transverse edge 37 of the absorption body 6 ends a greater distance from the front transverse edge 36 of the absorption body 6.

Figure 3:
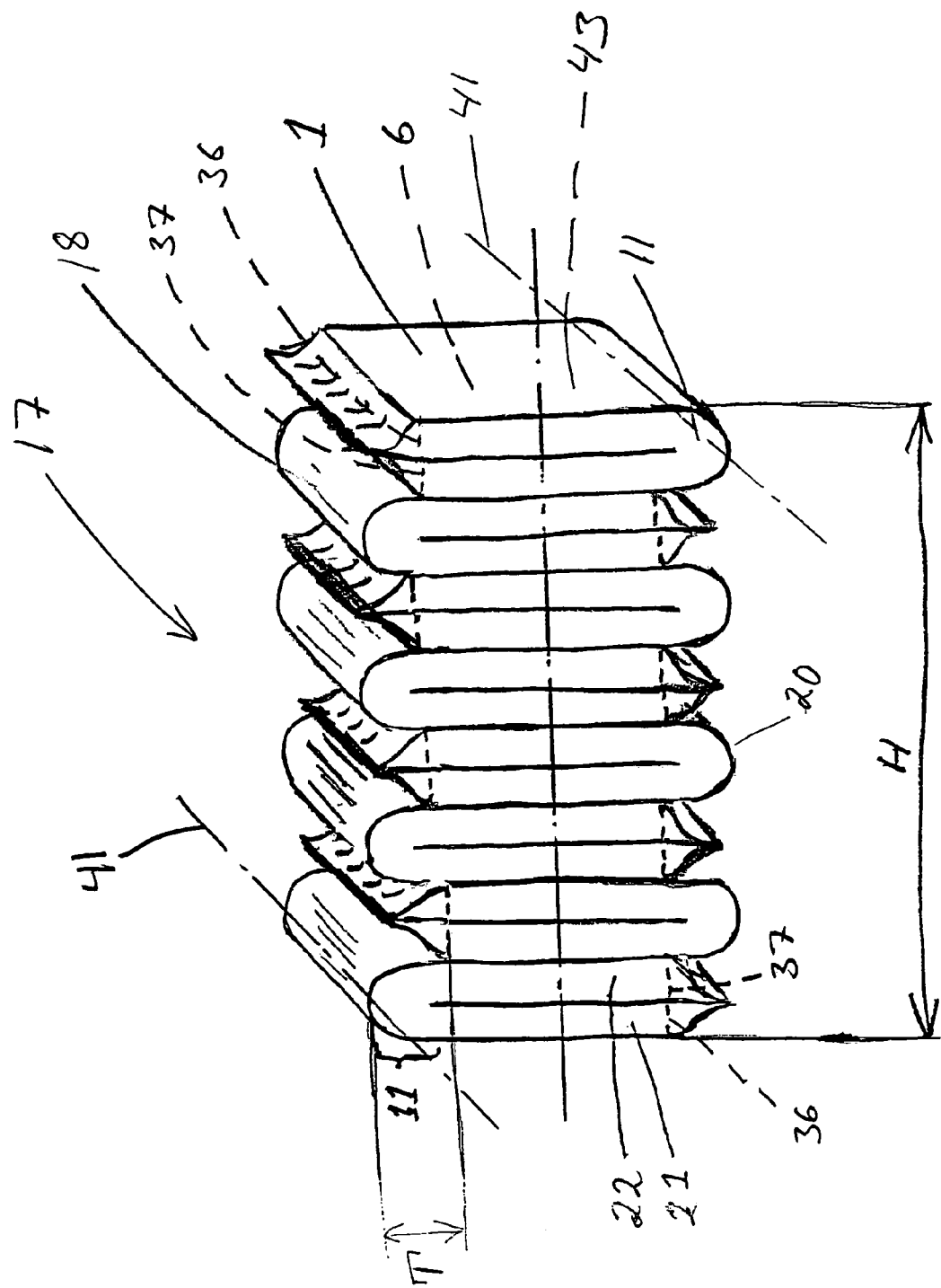
FIG. 3 shows a first preferred embodiment of a packaging unit according to the present invention.
Figure 4:
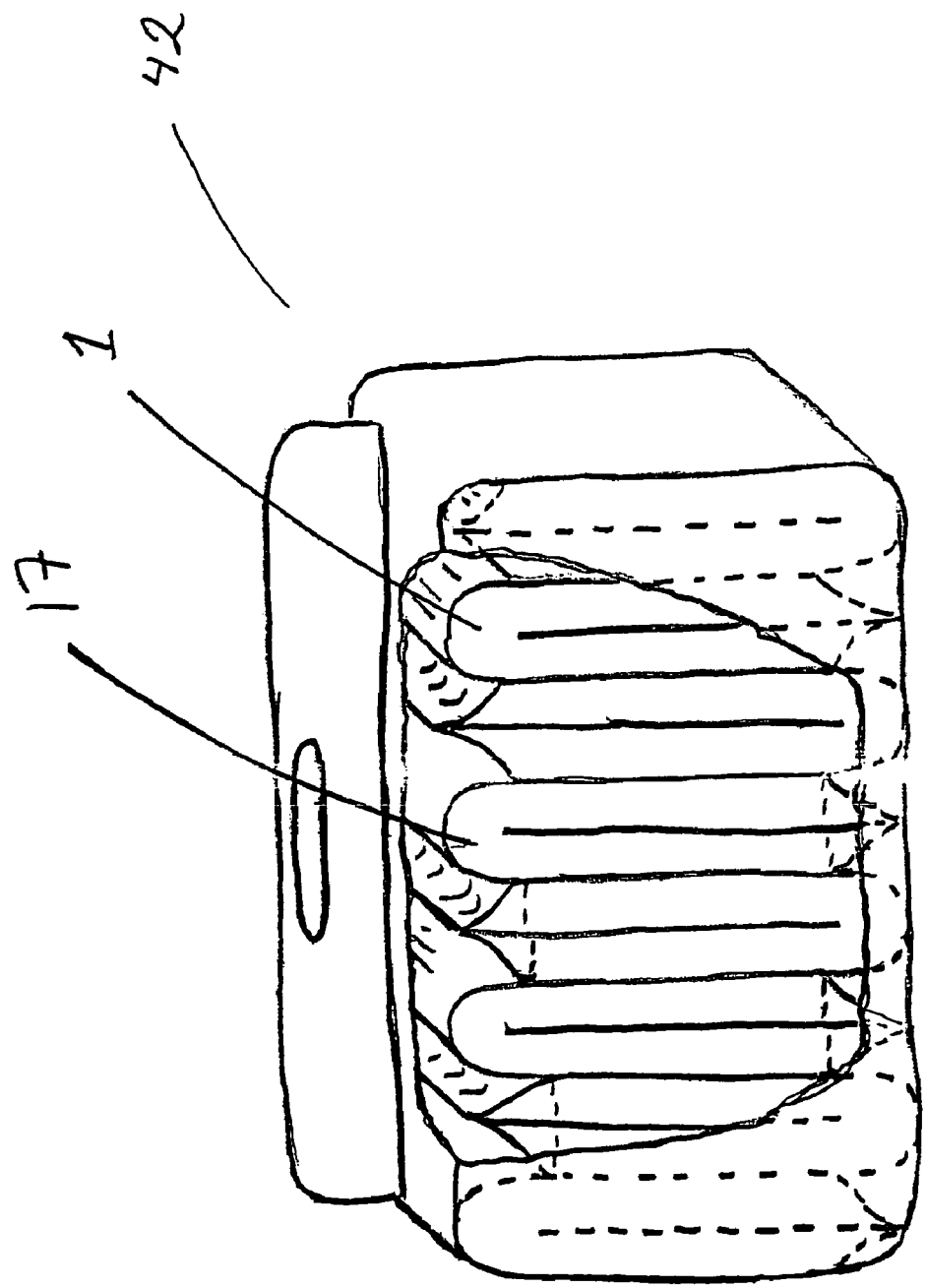
FIG. 4 shows a packaging comprising a packaging unit according to the present invention.

FIG. 3 shows how the diapers 1, folded according to FIG. 2, are configured in a packaging unit 17 according to a first embodiment of the invention, and FIG. 4 shows the packaging unit 17 introduced into a package 42. The packaging unit 17 comprises eight diapers 1, but it can of course alternatively contain a greater or smaller number of diapers 1.

The package 42 in FIG. 4 includes a plastic or paper bag and contains one packaging unit 17. In alternative embodiments, the package 42 can contain several packaging units 17 arranged side by side or on top of one another. It is also possible to have large packages 42 containing packaging units 17 arranged both side by side and in several layers on top of one another.

A packaging unit 42 can alternatively be enclosed in a band-shaped wrapper, as described in patent specification WO 93/16925, the content of which is hereby incorporated by reference. The packaging unit provided with the wrapper can then be enclosed in a bag of suitable material or can be supplied without any extra covering material.

It is also conceivable to vacuum-pack one or more packaging units 17 according to the invention in a substantially air-tight plastic package.

The packaging unit 17 comprises a first side 18, and a second side 20 arranged opposite the first side 18. The folded diapers 1 in the packaging unit 17 are oriented head to tail, that is to say every second diaper 1 is oriented with its fold area 11 arranged at the first side 18 of the packaging unit 17, and every other diaper 1 is oriented with its fold area 11 arranged at the second side 20 of the packaging unit 17. The front and rear end portions 21, 22 of every second diaper 1 are thus arranged at the first side 18 of the packaging unit 17, and the front and rear end portions 21, 22 of every other diaper are arranged at the second side 20 of the packaging unit 17. Consequently, the absorption bodies 6 of the diapers 1 are oriented head to tail, as clearly shown in FIG. 3.

The packaging unit 17 is further distinguished by the fact that the diapers 1 in the packaging unit 17 are offset in relation to one another at the first and second sides 18, 20 of the packaging unit 17. The diapers 1 are offset in the plane of the folded diapers 1, at right angles to the fold line 41 of the respective diaper 1. The diapers 1 arranged with their fold area 11 at the first surface 18 of the packaging unit 17 have been offset in a direction away from the second surface 20 of the packaging unit 17, and the diapers 1 arranged with their fold area 11 at the second surface 20 of the packaging unit 17 have been offset in a direction away from the first surface 18 of the packaging unit 17.

As shown in FIG. 3, the diapers 1 arranged head to tail in the packaging unit 17 have been offset in relation to one another so that the fold areas 11 of the diapers protrude outside the front and rear transverse edges 36, 37 of the absorption bodies 6 of adjacent diapers 1 oriented head to tail. The fold areas 11 of the diapers 1 in this case protrude by a distance T of about 5–30 mm, preferably 5–15 mm, outside the front and rear transverse edges 36, 37 of adjacent absorption bodies 6.

When the packaging unit 17 is to be introduced into a package 42, the stack of diapers 1 of the packaging unit 17 will be pressed together as much as possible in order to minimize the height H of the packaging unit and thus obtain a package which is as small as possible. At the same time, one will want to avoid permanent fold notches in the crotch portion of the diapers 1 upon compression.

The compression is effected at right angles to the material layers of the folded diapers 1, thus reducing the thickness of the diapers 1. The reduction in the thickness of the diapers largely comes from a reduction in the thickness of the absorption bodies 6.

By virtue of the fact that the diapers 1 are offset in relation to one another, the number of layers of absorption material 43 which will be compressed varies across the surface of the packaging unit 17. This can be put another way by saying that the number of front transverse edges 36 plus the number of rear transverse edges 37 of the absorption bodies 6 at the first or second side 18, 20 of the packaging unit 17 is equal to 0% of the number of fold areas 11 at the first or second side 18, 20 of the packaging unit 17.

At the central parts of the packaging unit 17, each diaper 1 has double layers of absorption material 43, and at both sides 18, 20 of the packaging unit only those diapers 1 comprising a fold area 11 at the side 18, 20 in question have double layers of absorption material 43.

Upon compression of the packaging unit 17, this method of configuring the diapers 1 in the packaging unit 17 means the central parts of the diapers 1 are, in principle, compressed twice as hard as those parts of the diapers 1 which are arranged at both sides 18, 20 of the packaging unit 17. Since the most sensitive parts of the diapers 1, namely the fold areas 11 of the diapers 1, are arranged at a respective side 18, 20, the method of arranging the diapers 1 in the packaging unit 17 means that it is possible to compress the packaging unit 17 considerably harder without creating permanent fold notches at the fold areas of the diapers. Increased compression means that the height H of the packaging unit 17 is reduced, while its width is slightly increased. However, the reduction in height H markedly exceeds the increase in width of the packaging unit 17, for which reason the total volume of the packaging unit 17 is decreased.

Figure 5:
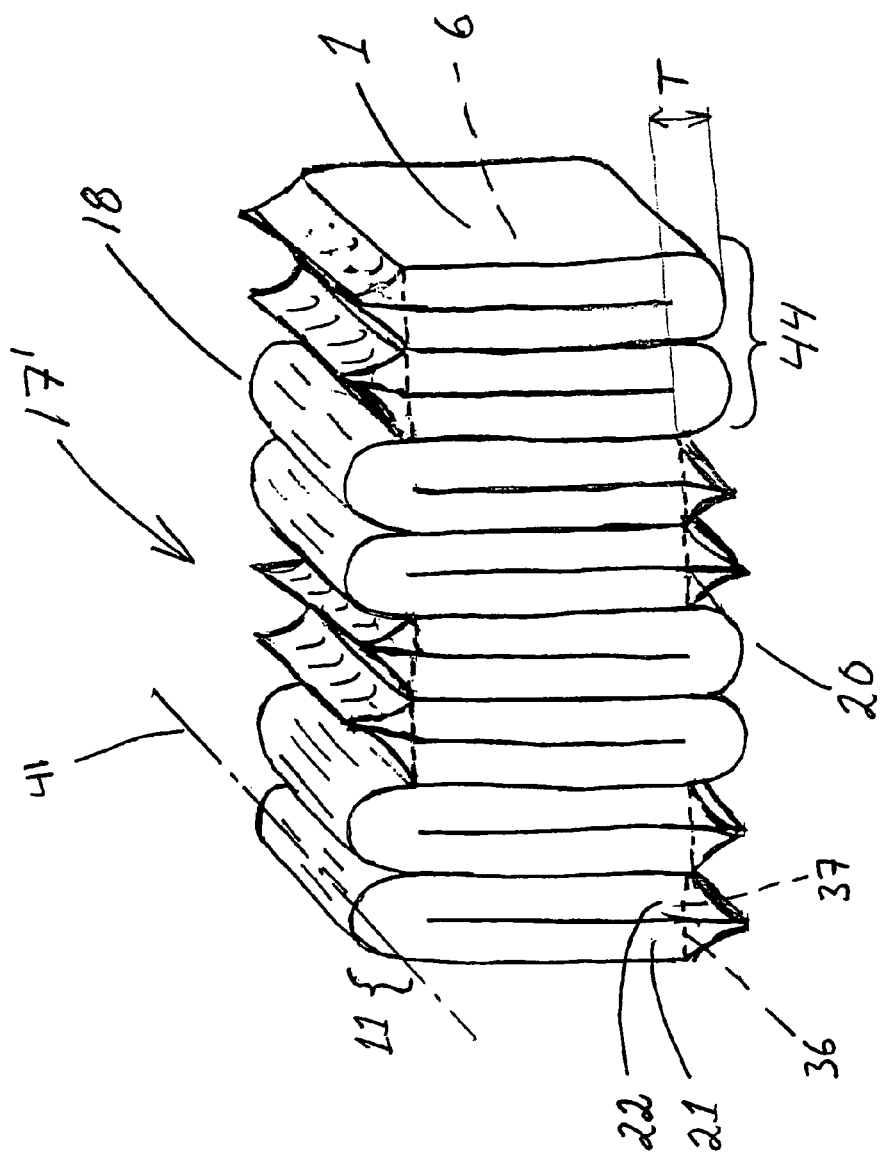
FIG. 5 shows a second preferred embodiment of a packaging unit according to the present invention.

FIG. 5 shows how the diapers are configured in a packaging unit 17' according to an alternative second embodiment of the invention. The packaging unit 17' contains eight diapers 1, but it can of course alternatively contain a greater or smaller number of diapers 1. The packaging unit 17' comprises a first side 18, and a second side 20 arranged opposite the first side 18.

The diapers 1 in the packaging unit 17' are arranged two by two in subunits 44, the diapers 1 in each individual subunit 44 being oriented with their fold areas at the same side 18, 20 of the packaging unit 17'. In alternative embodiments, each subunit 44 can contain three or four diapers 1, in which case all the diapers in each subunit 44 are oriented in the same direction.

The subunits 44 in the packaging unit 17' are oriented head to tail, that is to say every second subunit 44 is oriented with its two fold areas 11 arranged at the first side 18 of the packaging unit 17', and every other subunit 44 is oriented with its two fold areas 11 arranged at the second side 20 of the packaging unit 17'. In the respective subunits 44, the front and rear end portions 21, 22 of the diapers 1 are arranged at opposite sides 18, 20 of the packaging unit 17'.

The subunits 44 in the packaging unit 17' are offset in relation to one another at the first and second sides 18, 20 of the packaging unit 17'. Each subunit 44, comprising two diapers 1, is offset in the plane of the folded diapers 1, at right angles to the fold lines 41 of the diapers 1. The subunits 44 containing diapers 1 arranged with their fold areas 11 at the first surface 18 of the packaging unit 17' have been offset in a direction away from the second surface 20 of the packaging unit 17', and the subunits 44 containing diapers 1 arranged with their fold areas 11 at the second surface 20 of the packaging unit 17' have been offset in a direction away from the first surface 18 of the packaging unit 17'.

The subunits 44 arranged head to tail in the packaging unit 17' have been offset in relation to one another so that the fold areas 11 of the diapers 1 included in them protrude outside the front and rear transverse edges 36, 37 of the absorption bodies 6 of the diapers 1 belonging to the adjacent subunits 44 oriented head to tail. Consequently, in this embodiment too, the number of front transverse edges 36 plus the number of rear transverse edges 37 of the absorption bodies 6 at the first or second side 18, 20 of the packaging unit 17' is equal to 0% of the number of fold areas 11 at the first or second side 18, 20 of the packaging unit 17'.

The fold areas 11 in this case protrude by a distance T of about 5–30 mm, preferably 5–15 mm, outside the front and rear transverse edges 36, 37 of the absorption bodies 6 belonging to adjacent subunits 44.

When a packaging unit 17' according to this embodiment is to be introduced into a bag, or when a wrapper is to be applied around the packaging unit 17', this is done in the same way as for a packaging unit 17 according to first embodiment described above.

The most sensitive parts of the diapers 1, namely the fold areas 11 of the diapers 1, are protected from permanent fold notches by virtue of the fact that the fold area 11 of one of the diapers 1 included in a subunit 44 can expand in one direction, while the fold area of the other diaper 1 can expand in the opposite direction when the whole packaging unit is compressed.

Figure 6:
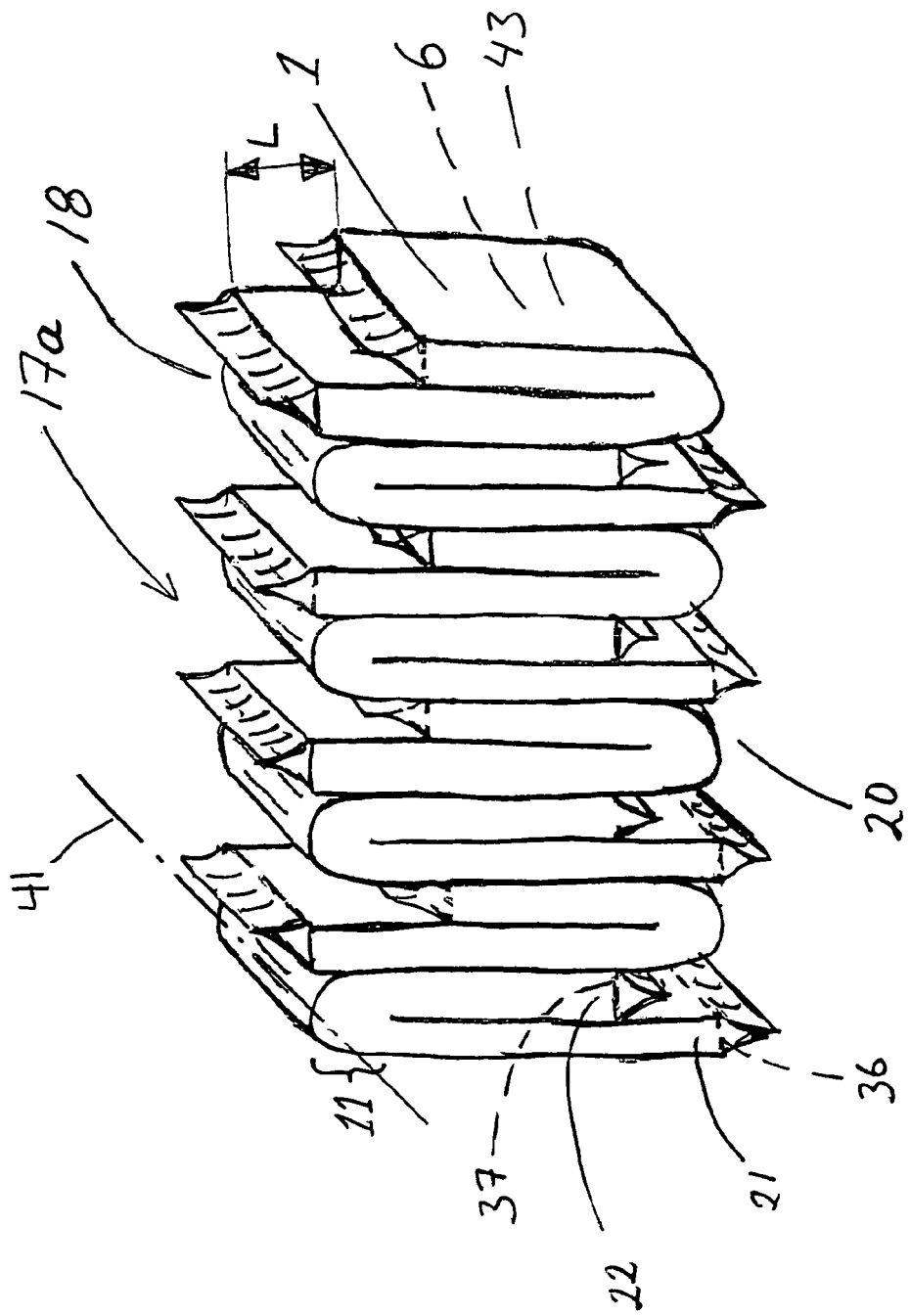
FIG. 6 shows a third preferred embodiment of a packaging unit according to the present invention.

FIG. 6 shows how the diapers 1 according to FIG. 2a are configured in a packaging unit 17a according to a third alternative embodiment of the invention. The packaging unit 17a contains eight diapers 1, but it can alternatively contain a greater or smaller number of diapers 1.

The packaging unit 17a comprises a first side 18, and a second side 20 arranged opposite the first side 18. The folded diapers 1 in the packaging unit 17a are oriented head to tail, that is to say every second diaper 1 is oriented with its fold area 11 arranged at the first side 18 of the packaging unit 17a, and every other diaper 1 is oriented with its fold area 11 arranged at the second side 20 of the packaging unit 17a. The front and rear end portions 21, 22 of every second diaper 1 are thus arranged at the first side 18 of the packaging unit 17a, and the front and rear end portions 21, 22 of every other diaper are arranged at the second side 20 of the packaging unit 17a.

Each diaper 1 is folded along a transverse line 41 arranged at a distance, in the longitudinal direction, from the transverse midline of the diaper 1. The folding is arranged such that the distance L between the front and rear transverse edges 36, 37 of the absorption body 6 is about 5–30 mm, preferably 5–15 mm, in the longitudinal direction of the respective diaper 1. Because the front transverse edge 36 and rear transverse edge 37 of the absorption bodies 6 are offset in relation to one another, the packaging unit 17a has only three-quarters the number of layers of absorption material 43, at the first or second side 18, 20 of the packaging unit 17a, as there are in the central parts of the packaging unit.

To express this another way, the number of front transverse edges 36 plus the number of rear transverse edges 37 of the absorption bodies 6 at the first and second sides 18, 20 of the packaging unit 17a is the same, that is to say 100%, as the number of fold areas 11 at the first and second sides 18, 20 of the packaging unit 17a.

Upon compression of the packaging unit 17a, this method of configuring the diapers 1 in the packaging unit 17a means that the central parts of the diapers 1 are compressed harder than those parts of the diapers 1 which are arranged at both sides 18, 20 of the packaging unit 17a. The diapers 1 can thus be compressed considerably harder since the most sensitive parts of the diapers 1, namely the fold areas 11, are not compressed as hard as the other parts of the diapers 1.

The invention also includes all conceivable combinations of the preferred embodiments described.

Moreover, the invention is not limited to the above-mentioned preferred embodiments, or the construction of the exemplary diaper above, and instead it can of course be applied to other embodiments within the scope of the attached patent claims.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A packaging unit having a first side and an opposite second side, the packaging unit comprising:
    a plurality of folded absorbent articles, each absorbent article having a front end portion, a rear end portion, and a crotch portion arranged between the end portions, each absorbent article further comprising an absorption body comprising a front transverse edge arranged at the front end portion of the article, and a rear transverse edge arranged at the rear end portion of the article, each article being folded along a substantially transverse fold line arranged in the crotch portion so as to form a fold area, and
    wherein some of said folded absorbent articles are oriented with said fold areas at the first side of the packaging unit, and some of said folded absorbent articles in the packaging unit are oriented with their fold areas at the second side of the packaging unit,
    wherein a sum of the front transverse edges and the rear transverse edges disposed at the first side of the packaging unit is at most equal to 100% of the number of said fold areas at the first side of the packaging unit,
    wherein a sum of the front transverse edges and the rear transverse edges at the second side of the packaging unit is at most equal to 100% of the number of fold areas at the second side of the packaging unit; and
    wherein articles arranged with their fold lines at the first side of the packaging unit are offset by a distance of about 5–30 mm in relation to articles arranged with their fold lines at the second side of the packaging unit.

2. A packaging unit according to claim 1, wherein said absorbent articles in the packaging unit are folded about substantially transverse fold lines arranged substantially at the centre of the absorption bodies in a longitudinal direction of the absorption bodies, some of said articles being oriented with their substantially transverse fold lines at the first side of the packaging unit being offset in a direction away from the second side of the packaging unit, and some of said articles being oriented with their substantially transverse fold lines at the second side of the packaging unit being offset in a direction away from the first side of the packaging unit.

3. A packaging unit according to claim 1, wherein said plurality of absorbent articles in the packaging unit are folded about substantially transverse fold lines situated at a distance from the centre of the absorption bodies in the longitudinal direction of the absorption bodies, only one of the front transverse edge and rear transverse edge of the respective article being arranged at either the first or second side of the packaging unit.

4. A packaging unit according to claim 1, wherein every second folded article is oriented with its substantially transverse fold line at the first side of the packaging unit, and every other folded article is oriented with its substantially transverse fold line at the second side of the packaging unit.

5. A packaging unit according to claim 1, wherein a plurality of said folded absorbent articles are arranged in subunits, all the articles in a subunit being arranged with their substantially transverse fold lines at the same side in the packaging unit, and subunits adjacent to one another being arranged with the substantially transverse fold lines of their articles at different sides of the packaging unit.

6. A packaging unit according to claim 5, wherein each subunit comprises two to four articles.

7. A packaging unit according to claim 6, wherein each subunit comprises two articles.

8. A packaging unit according to claim 1, wherein articles arranged with their fold lines at the first side of the packaging unit are offset by a distance of 5–15 mm in relation to articles arranged with their fold lines at the second side of the packaging unit.

9. A packaging unit according to claim 3, wherein the substantially transverse fold lines of the articles are situated at a distance from the centre of the absorption bodies in the longitudinal direction of the absorption bodies, so that the distance between the front transverse edge and the rear transverse edge of the absorption bodies is about 5–30 mm, when the article is folded.

10. A packaging unit according to claim 9, wherein the substantially transverse fold lines of the articles are situated at a distance from the centre of the absorption bodies in the longitudinal direction of the absorption bodies, so that the distance between the front transverse edge and the rear transverse edge of the absorption bodies is 5–15 mm, when the article is folded.

11. A packaging unit according to claim 1, wherein the packaging unit is packed in a bag.

12. (Original) A packaging unit according to claim 1, wherein the packaging unit is surrounded by a wrapper.

13. A packaging unit according to claim 1, wherein the packaging unit contains babies' diapers.

14. A packaging unit according to claim 1, wherein the packaging unit contains incontinence diapers.

15. A packaging unit having a first side and an opposite second side, the packaging unit comprising:

a plurality of folded absorbent articles, each absorbent article having a front end portion, a rear end portion, and a crotch portion arranged between the end portions, each absorbent article further comprising an absorption body comprising a front transverse edge arranged at the front end portion of the article, and a rear transverse edge arranged at the rear end portion of the article, each article being folded along a substantially transverse fold line arranged in the crotch portion so as to form a fold area, and wherein some of said folded absorbent articles are oriented with said fold areas at the first side of the packaging unit, and some of said folded absorbent articles in the packaging unit are oriented with their fold areas at the second side of the packaging unit, wherein a sum of the front transverse edges and the rear transverse edges disposed at the first side of the packaging unit is at most equal to 100% of the number of said fold areas at the first side of the packaging unit, wherein a sum of the front transverse edges and the rear transverse edges at the second side of the packaging unit is at most equal to 100% of the number of fold areas at the second side of the packaging unit; and wherein said plurality of absorbent articles in the packaging unit are folded about substantially transverse fold lines situated at a distance from the centre of the absorption bodies in the longitudinal direction of the absorption bodies, only one of the front transverse edge and rear transverse edge of the respective article being arranged at either the first or second side of the packaging unit.

16. A packaging unit according to claim 15, wherein the substantially transverse fold lines of the articles are situated at a distance from the centre of the absorption bodies in the longitudinal direction of the absorption bodies, so that the distance between the front transverse edge and the rear transverse edge of the absorption bodies is about 5–30 mm, when the article is folded.

17. A packaging unit according to claim 16, wherein the substantially transverse fold lines of the articles are situated at a distance from the centre of the absorption bodies in the longitudinal direction of the absorption bodies, so that the distance between the front transverse edge and the rear transverse edge of the absorption bodies is 5–15 mm, when the article is folded.

* * * * *